(12) United States Patent
Wu

(10) Patent No.: US 6,450,967 B1
(45) Date of Patent: Sep. 17, 2002

(54) MEASURING METHOD FOR ANAEROBIC THRESHOLD

(75) Inventor: Mu-Chuan Wu, Tainan Hsien (TW)

(73) Assignee: Tonic Fitness Technology, Inc., Tainan Hsien (TW)

( * ) Notice: Subject to any disclaimer, the term of this patent is extended or adjusted under 35 U.S.C. 154(b) by 0 days.

(21) Appl. No.: 09/884,042

(22) Filed: Jun. 20, 2001

(51) Int. Cl.[7] .................................................. A61B 5/00
(52) U.S. Cl. ...................................... 600/500; 600/485
(58) Field of Search .......................... 600/300, 519–521, 600/481, 485, 500

(56) References Cited

U.S. PATENT DOCUMENTS

| | | | | |
|---|---|---|---|---|
| 5,810,722 A | * | 9/1998 | Heikkila | 600/520 |
| 6,104,947 A | * | 8/2000 | Heikkola et al. | 600/519 |
| 6,174,289 B1 | * | 1/2001 | Binder | 600/520 |
| 6,241,684 B1 | * | 1/2001 | Amano et al. | 600/529 |

* cited by examiner

Primary Examiner—Robert L. Nasser
(74) Attorney, Agent, or Firm—Bacon & Thomas, PLLC

(57) ABSTRACT

A measuring method for anaerobic threshold (AT) includes a plurality of steps carried out by a data putting-in unit, a load class selecting unit, a detecting and calculating unit and a display unit. The steps includes putting in age, weight and gender of a user wearing a heart beat emitter and using an exercise device (for example, a treadmill) mounted with those units, and selecting a load class to take exercise on the exercise device. Then those units detect, measure and record heart beat cycle and calculate heart beat cycle difference detected for every set period of time. Then AT limit point is found out and displayed on the display unit for reference for the user to control exercise load and time.

3 Claims, 4 Drawing Sheets

| Name | Formula |
|---|---|
| (A) the highest heart beat value ($HR_{limit}$) | $(220 - age - HR_{rest}) \times K1 + HR_{rest}$<br>Remark 1. $HR_{rest}$ is heart beat value during rest.<br>Remark 2. $K_2$ is a constant. |
| (B) Basal Metabolic Rate (L/min) | Body weight(kg) × 3.5(ml/kg/min) ÷ 1000 |
| (C) Maximal Heart Rate (bpm) | 220-age<br>Remark 1. bpm is the heart beat number per minute |
| (D) AT $VO_2$(L/min) | [AT power value (Rate watts) × $K_2$] ÷ 5.047 + basal metabolic rate.<br>Remark 1. $K_2$ is a constant.<br>Remark 2. One liter oxygen = 5.047 kcal. |
| (E) AT $VO_2$(ml/kg/min) | AT $VO_2$(L/min) ÷ body weight(Kg) |
| (F) $VO_2$ max(L/min) | [Maximum power value (Rate watts) × $K_2$] ÷ 5.047 + basal metabolic rate. |
| (G) $VO_2$ max(ml/Kg/min) | $VO_2$ max(L/min) ÷ body weight(Kg) |

*FIG. 4*

MEASURING METHOD FOR ANAEROBIC THRESHOLD

BACKGROUND OF THE INVENTION

This invention relates to a measuring method for anaerobic threshold by detecting and analyzing heart beat during physical exercise, particularly to one possible to detect the best exercise strength of a physical exerciser to maintain stable condition in physical exercise as a reference basis for adjusting training of exercise.

Anaerobic Threshold (AT) is publicly considered to be one of the best and the most important reference for exercise training effect. And it is described in detail in a book called "Manual for experiment of exercise physiology" by Mr. Lin Cheng Chang, professor of National Taiwan Normal University, and described in page 219 of the book. In 1981 Mr. Moritani and his colleagues made use of the idea of critical power for training in riding a bike (Moritaki T., A. Nagata, H. A. Devries and M. Muro, "Critical power as a measure of physical work capacity and anaerobic threshold." Egonomics, pages 5, 24, 339–350, 1981). Further in 1984, Mr. Hughson and his colleagues made use of the same idea for training on a treadmill, explaining about running speed for continual long time (with speed limit), and proving critical power being worthy for physical exercise and training (in "A high velocity treadmill running test to assess endurance running potential", International Journal of Sport Medicine, pages 5, 23–25, 1984 by Hughson R. L., C. J. Orok and L. E. Staudt). And in 1992, Mr. Wakayoshi and his colleagues have found out that relative percentage of anaerobic threshold and critical power is 0.818, practically not a conspicuous difference between them (in "Determination and validity of critical velocity as an index of swimming performance in the competitive swimmer", Europe Journal of Applied Physiology, by Wakayoshi K., L. Ikuta, T. Yoshita, M. Udo, T. Moritani, Y. Mutoh, Miyashita, pages 64, 153–157, 1992).

In fact, anaerobic threshold serves not only as a reference but also as an important reference basis for avoiding exercise harm and injury. Because when an athlete makes exercise beyond anaerobic threshold, waste produced in the athlete's body by physical exercise begins to accumulate and liable to give rise to exercise harm or injury. Therefore, anaerobic threshold is a critical standard for exercise effect and a warning signal to avoid exercise harm or injury.

However, very costly equipment is needed for measuring anaerobic threshold to understand in an early period of critical power of an athlete, necessary to test by practical exercise, and then blood test in conjunction with expensive instruments to find out anaerobic threshold. Thus, it is obvious that considerable expenditure and long waiting (maybe for a few hours) are needed to understand critical power of an athlete or sportsman. So athletes and sportsmen cannot get applicable gains in daily training. In view of proof of Professor Moritani that anaerobic threshold can be measured by detecting and analyzing heart beat during physical exercise, based on statistics of clinical tests, this applicant has invented a measuring method for anaerobic threshold by utilizing mathematics and electronic technology and using a calculating and a displaying device mounted on a training device such as a treadmill, a stationary bike, etc, offering athletes and sportsman test of anaerobic threshold and suggestion for proper exercise without need of using blood test.

SUMMARY OF THE INVENTION

The objective of the invention is to offer a measuring method for anaerobic threshold by testing and analyzing heart beat special data, without using blood test to find out quickly anaerobic threshold value.

BRIEF DESCRIPTION OF DRAWINGS

This invention will be better understood the invention by referring to the accompanying drawings, wherein.

DETAILED DESCRIPTION OF THE PREFERRED EMBODIMENT

Figure 1:
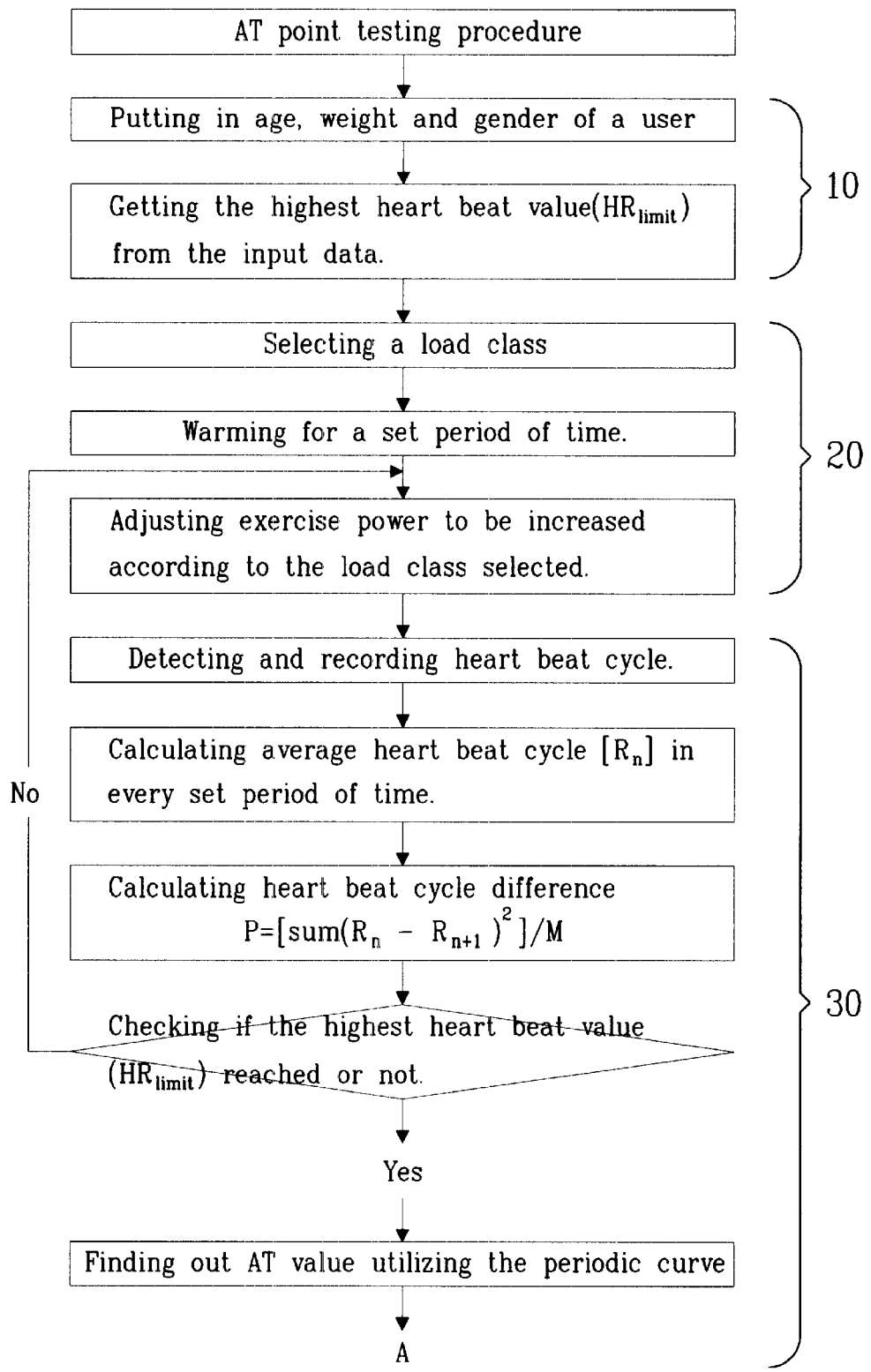
FIG. 1 is a flow chart of a measuring method for anaerobic threshold in the present invention.
Figure 2:
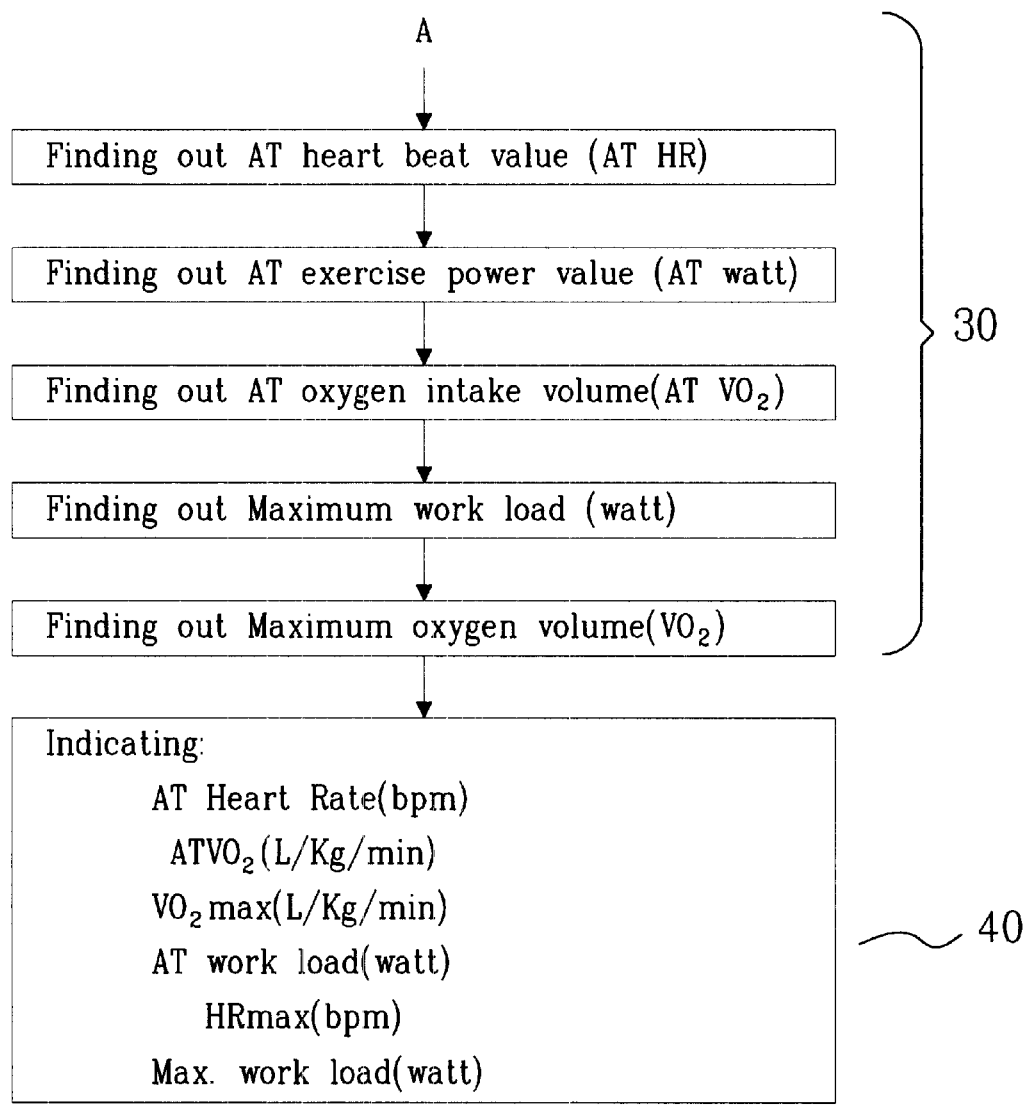
FIG. 2 is another flow chart of the measuring method for anaerobic threshold in the present invention.

A preferred embodiment of a measuring method for anaerobic threshold in the present invention, as shown in FIGS. 1 and 2, includes a data input step carried out by a data putting-in unit 10 to decide the highest heart beat rate according to the age, the weight and the gender of a user put in. The method further includes a second step of selecting a load class by using a load class selecting unit 20, which has five load classes 0–4. Each load class consists of a first warming-up stage and a second load increasing stage. The first stage of warming-up stage has a constant load and a set period of time for warming-up, and when finishing the warming-up stage, next comes the second load increasing stage. In the second load increasing stage a preset load is added after every preset period of time, increasing the load in a steady rise.

Then the method includes a third step of detecting and recording heart beat and the exercise load of a user taking exercise on the exercise device by means of a detect and calculate unit 30, which calculates out the limit point of anaerobic threshold (AT) value.

Further, the method includes a fourth step of displaying the data got from the detect and calculate unit 30, such as AT heart beat value, At exercise power value, AT oxygen intake, the maximum exercise power, the maximum oxygen intake, etc.

Next, testing steps of the anaerobic threshold (AT) value is described as below.

(1) Starting testing procedure of anaerobic threshold (AT) value.

(2) Putting in the age, the weight and the gender of a user (athlete or sportsman) in the data putting-in unit 10 fixed on an exercise device and then pressing a confirm key, then the highest heat beat value ($HR_{limit}$) is got by the exercise device according to the data input. The formula is shown in (a) in FIG. 4.

(3) Next, the user selects a load class in accordance with the personal capacity on the load class selecting unit 20 having five load classes 0–4. The lower the class, the lower the exercise power. At the same time a user wears a heart beat emitter, and then the receiver provided in the exercise device may receive the heart beat signal of the user.

(4) Next, the user stands on the exercise device (such as a stationary bike, a treadmill, etc.) and begins the exercise procedure by starting to make warming-up exercise for a set period of time on the exercise device. After the set period of time passed, the load is to be added after every set period of time (for example, one or two minute, etc.). If the load class is "0", the load is $W_1$. Then a load $W_2$ is to be added after every set period of time, namely, the first set period of time has the load $W_1+W_2$, the second set period of time has the load $W_1+2W_2$, and so on.

(5) The detect and calculate unit 30 at the same time detects, calculates and records heart beat cycle of the user, calculating average hart beat cycle "$R_n$" in every set period of time, and also hart beat cycle difference $P=[\text{sum } (R_{n-Rn+1})^2]/M$ (M is the heart beat cycle in every set period of time, T seconds minus 1). In simple words, if test finishes 4×T time, it means that 4 of T time cycles passed, or the M rate is 4 cycles minus 1, equivalent to 3 (M=4−1=3).

Figure 3:
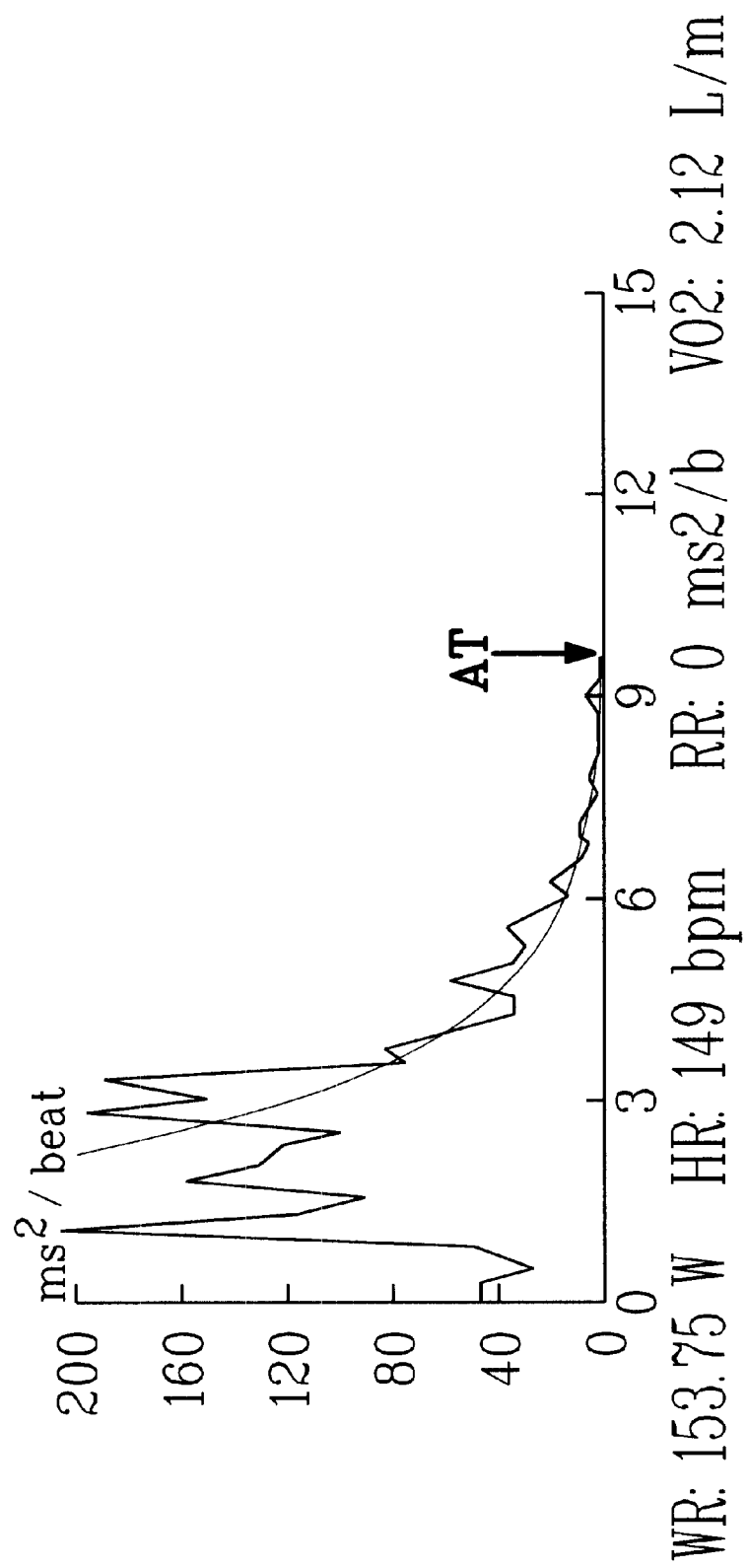
FIG. 3 is a periodical curved got by the measuring method for anaerobic threshold in the present invention; and, FIG. 4 is a formula used in the measuring method for anaerobic threshold in the present invention.

(6) Then the exercise device synchronously tests if the user has reached the highest heart beat value ($HR_{limit}$). If the user has not reached yet the highest heart beat rate (its calculating formula is shown in (A) in FIG. 4), the user returns to the (5) step in FIG. 5, continuing to exercise with a increased load by selecting a load class. On the contrary, if the user has reached the highest heart beat rate, the user may calculate AT value according to the periodical curve (as shown in FIG. 3, AT is the point "0" of the inclining curve). The periodical curve shows curved alteration of heart beat cycle difference by the rate got from testing the user taking exercise for a set period of time. The left side area of AT is belonged to an aerobic area, wherein aerobic exercise is made for rehabilitating of heart disease, reducing fat, and strengthening function of heart and lung. The right side area of AT is belonged to an anaerobic area, wherein anaerobic exercise is made. As anaerobic exercise may lead to accumulation of lactic acid, produce $CO_2$ and body heat, it cannot continue very long, but can strengthen muscle, instant force and muscle strength (or beauty) of the user, and accordingly is necessary for training. So AT value is the watershed of the aerobic area and the anaerobic area.

(7) AT heart beat rate (ATHR, or heart beat rate at the time of exercise) can be got from the periodic curve mentioned above, and AT exercise power rate (AT watt or AT at the exercising moment), and AT oxygen intake rate (AT $VO_2$) can be got from the formula shown in (D) in FIG. 4. And the maximum work load (watt) and the maximum oxygen intake ($VO_2$max) are got from the formula shown in (F) in FIG. 4. .

(8) The display unit fixed on the exercise device finally indicates:
  1. AT Heart Beat Rate (bpm), i.e. heart beat rate at the point of AT.
  2. AT $VO_2$(L/K/min), its formula shown in (E) in FIG. 4.
  3. $VO_2$max(L/KG/min, its formula shown in (G) in FIG. 4.
  4. AT work load (watt), i.e. the exercise power rate at the AT point.
  5. HR max (bpm),. its formula shown in C in FIG. 4, i.e. the largest heart beat.
  6. Max. work load(watt), i.e. the largest exercise power rate.

The bpm is heartbeat per minute.

As can be understood from the aforesaid description, the measuring method for AT in the invention may measure out information about At of an exerciser, an athlete or a sportsman in a very short time during taking exercise on a exercise device, such as the power limit of the exerciser, a very critical reference for him/her. The measuring method is helpful to an exerciser, an athlete or a sportsman in realizing his/her own body condition during exercise, and useful for a trainer to arrange a training course for an exerciser, an athlete or a sportsman. Moreover, the method can save more time than the conventional blood test involving costly instruments needed.

While the preferred embodiment of the invention has been described above, it will be recognized and understood that various modifications may be made therein and the appended claims are intended to cover all such modifications that may fall within the spirit and scope of the invention.

I claim:

1. A measuring method for anaerobic threshold by detecting and analyzing heart beat data, wherein said measuring method is accomplished by a data putting-in unit, a load class selecting unit, a detecting and calculating unit and a display unit, said measuring method comprising the steps of:

(1) starting a test procedure for determining an anaerobic threshold;
  (2) inputting data for age, weight and gender of a user in said data putting-in unit mounted on an exercise device, said data putting-in unit supplying the highest heart beat rate;
  (3) the user selecting one of a plurality of load classes set in said load class selecting unit and wearing a heart beat emitter, said heart beat emitter transmitting heart beat of the user to a receiver mounted on said exercise device;
  (4) the user standing on said exercise device and beginning to take warming-up exercise according to the load class the user selected;
  (5) the exercise device adjusting an increasing rate of exercise power, based on the load class selected by the user after the user finished the warming-up exercise, in order to gradually increase exercise load;
  (6) at the same time said detecting and calculating unit mounted on the exercise device, detects and records the user's heart beat cycle produced during exercise, said detecting and calculating unit calculates the average heart beat cycle in every set period of time and calculates the difference in the heart beat cycle; and,
  (7) said heart beat cycle difference is compared with said maximum heart beat, a periodical curve is produced by alteration of said heart beat cycle difference of the user, an anaerobic threshold (AT) rate is derived by utilizing said periodical curve, and said anaerobic threshold rate is displayed on said display unit for reference.

2. The measuring method for anaerobic threshold as claimed in claim 1, wherein said load class selecting unit has a plurality of load classes, and each load class having a first warming-up stage and a second load increasing stage, said second load increasing stage increasing a preset load for every set period of time.

3. The measuring method for anaerobic threshold as claimed in claim 1, wherein said display unit indicates At value, AT exercise power value, AT oxygen intake quantity, the largest exercise power value, the largest oxygen intake quantity, and largest heart beat value supplied by said detecting and calculating unit.

* * * * *